(12) United States Patent
Hoffmann

(10) Patent No.: US 6,793,815 B2
(45) Date of Patent: Sep. 21, 2004

(54) PUMPING ARRANGEMENT

(75) Inventor: Bernd Hoffmann, Karlsruhe (DE)

(73) Assignee: Agilent Technologies, Inc., Palo Alto, CA (US)

( * ) Notice: Subject to any disclaimer, the term of this patent is extended or adjusted under 35 U.S.C. 154(b) by 77 days.

(21) Appl. No.: 10/336,310

(22) Filed: Jan. 3, 2003

(65) Prior Publication Data

US 2004/0000510 A1 Jan. 1, 2004

(30) Foreign Application Priority Data

Jun. 29, 2002 (EP) .......................................... 02014478

(51) Int. Cl.[7] .............................................. B01D 15/08
(52) U.S. Cl. ..................... 210/198.2; 210/101; 210/656
(58) Field of Search ................................ 210/635, 656, 210/659, 101, 143, 198.2

(56) References Cited

U.S. PATENT DOCUMENTS

| | | | | |
|---|---|---|---|---|
| 3,712,513 A | * | 1/1973 | Ashmead et al. | 222/134 |
| 4,311,586 A | * | 1/1982 | Baldwin et al. | 210/101 |
| 4,475,821 A | * | 10/1984 | Koch et al. | 366/160.1 |
| 4,478,713 A | * | 10/1984 | Girot et al. | 210/101 |
| 4,506,987 A | * | 3/1985 | Daughton et al. | 366/160.3 |
| 4,595,495 A | * | 6/1986 | Yotam et al. | 210/101 |
| 4,595,496 A | * | 6/1986 | Carson | 210/101 |
| 4,714,545 A | * | 12/1987 | Bente et al. | 210/101 |
| 4,728,434 A | * | 3/1988 | Trafford | 210/656 |
| 4,879,029 A | * | 11/1989 | Whitehead | 210/198.2 |
| 4,980,059 A | * | 12/1990 | Barlow et al. | 210/198.2 |
| 4,981,597 A | * | 1/1991 | Allington et al. | 210/656 |
| 4,994,180 A | * | 2/1991 | Sims et al. | 210/198.2 |
| 5,112,492 A | | 5/1992 | Ransohoff | 210/656 |
| 5,607,581 A | | 3/1997 | Gerner et al. | 210/198.2 |
| 6,228,153 B1 | | 5/2001 | Saitoh | 96/218 |

FOREIGN PATENT DOCUMENTS

DE  40 41 433  6/1992  .............. 210/198.2

OTHER PUBLICATIONS

Zinngrebe, U., Examiner, European Search Report EP 02 01 4478 dated Oct. 23, 2002.

* cited by examiner

*Primary Examiner*—Ernest G. Therkorn

(57) ABSTRACT

A pumping arrangement, for example for liquid chromatography, includes a first liquid reservoir at a first height level, connected via a first hydraulic path to a pumping device; a second liquid reservoir at a second height level, connected via a second hydraulic path to the pumping device; and filtration devices arranged in the first and in the second hydraulic path. Each filtration device includes an outer member forming a first chamber, and an inner member arranged within the outer member and forming a second chamber. The inner member is porous and acts as a filter for liquid flowing from the first chamber to the second chamber. The arrangement ensures efficient filtering and prevents undesired backflow of liquid.

9 Claims, 2 Drawing Sheets

PUMPING ARRANGEMENT

The invention relates to a pumping arrangement, for example for liquid, chromatography, wherein liquids from two or more reservoirs are delivered to an hydraulic resistance, such as a chromatographic separation column. Such a pumping arrangement can be used, for example, for gradient operation in preparative liquid chromatography.

BACKGROUND OF THE INVENTION

High performance liquid chromatography (HPLC) is a well-known and widespread chromatographic technique to separate and analyze liquid samples containing different compounds of interest. The methodology of HPLC can be divided into two areas: analytical and preparative scale liquid chromatography.

The difference is reflected in the instrumentation setup, which typically consists of a liquid pump, an injection module, one or more chromatographic separation columns, at least one detection module, and in preparative liquid chromatography, always one or several fraction collection devices.

Analytical scale HPLC pumps are typically working in the flow rate range of 1–5 ml/min. They use active pump valves. In most cases the inlet or outlet valve has a spring support so that the liquid path in the pump head is actively closed at no flow conditions. Thus, in a gradient system consisting of multi channel pump modules, undesired mixing of different solvents will be prevented.

HPLC pumps working at flow rates above 10 ml/min up to several hundred ml/min do not have active pump valves.

In order to achieve precise gradients at high flow rates, various conditions with regard to liquid handling have to be fulfilled:

Three very important aspects, which are also addressed in the present invention, are as follows:

a) Filtration of liquids at high flow rates.
b) Handling of liquid flow when using high volume liquid containers at different storage levels in a laboratory.
c) Management of the liquid priming process.

With regard to the mentioned aspects a) to c), the prior art and the problems encountered are as follows:

a) Filtration of liquids at high flow rates is important in order to prevent access of fades or other small impurities that could enter into the pump head. They can prevent proper valve sealing, causing flow irregularities. Furthermore they may increase the system pressure over time, due to plugging of instrumental parts or the column inlet itself. Most often inlet filters made out of sintered metal are used. Over time they are prone to become rusty or they may plug very soon because of their limited free surface area and thus their overall reduced capacity. In practice they are prone to error and have to be replaced very often. With bioanalytical applications, such as the separation of proteins, stainless steel filtration devices are not the matter of choice because of possible protein-metal interaction processes.
b) High flow HPLC pumps require plungers having much greater cross section than analytical pumps. As a matter of fact such plungers cause cavitations within the valves very easily and will destroy the ball seat as well as the ball itself in a very short period of time. In this case manual stop valves are used for interactive work to prevent undesired crossflow between liquid containers at different storage levels. For routine and automatic controlled systems electrically controlled stop valves are used. However, they are expensive and limited in lifetime.
c) Priming high flow HPLC instrumentation is of general importance. This can be done by cumbersome manual sucking the air volume out of the tubing with a syringe. This, however, is very inconvenient and time-consuming for the chromatographer.

SUMMARY OF THE INVENTION

It is thus an object of the invention to provide a pumping arrangement, which avoids the problems and disadvantages of the prior art.

Specifically, it is an object of the invention to provide a pumping arrangement with an improved filtering device having increased lifetime and filtering efficiency.

It is a further object to prevent uncontrolled cross flow in case that liquid reservoirs are stored at different height levels.

The pumping arrangement of the invention comprises:

a first liquid reservoir at a first height level, connected via a first hydraulic path to a pumping means;
a second liquid reservoir at a second height level, connected via a second hydraulic path to the pumping means; and
first and second filtration devices arranged in the first and second hydraulic path, respectively, wherein each filtration device comprises an outer member forming a first chamber, and an inner member arranged within the outer member and forming a second chamber, with the inner member being porous for allowing liquid flow from the first chamber to the second chamber.

The invention has the additional advantages that it is particularly suitable for handling non-degassed solvents and for the liquid priming process. One of the characteristics of the present invention is that the filtration device embodies several functions in one device, such as the filtering function and the prevention of undesired backflow.

According to a preferred embodiment of the invention the filtration devices are arranged at the same height level. In a further preferred embodiment, the first (outer) chamber of the filtration device accommodates a two-phase system comprising liquid from a liquid reservoir and vapor of this liquid.

It is another advantage of the invention that the filtration device can be reused after blockage by impurities, since it can easily be cleaned, for example with ultrasound cleaning. Furthermore the filtration device can easily be sterilized before use.

BRIEF DESCRIPTION OF THE DRAWINGS

In the following embodiments of the invention will be explained with reference to the drawings.

DETAILED DESCRIPTION

Figure 1:
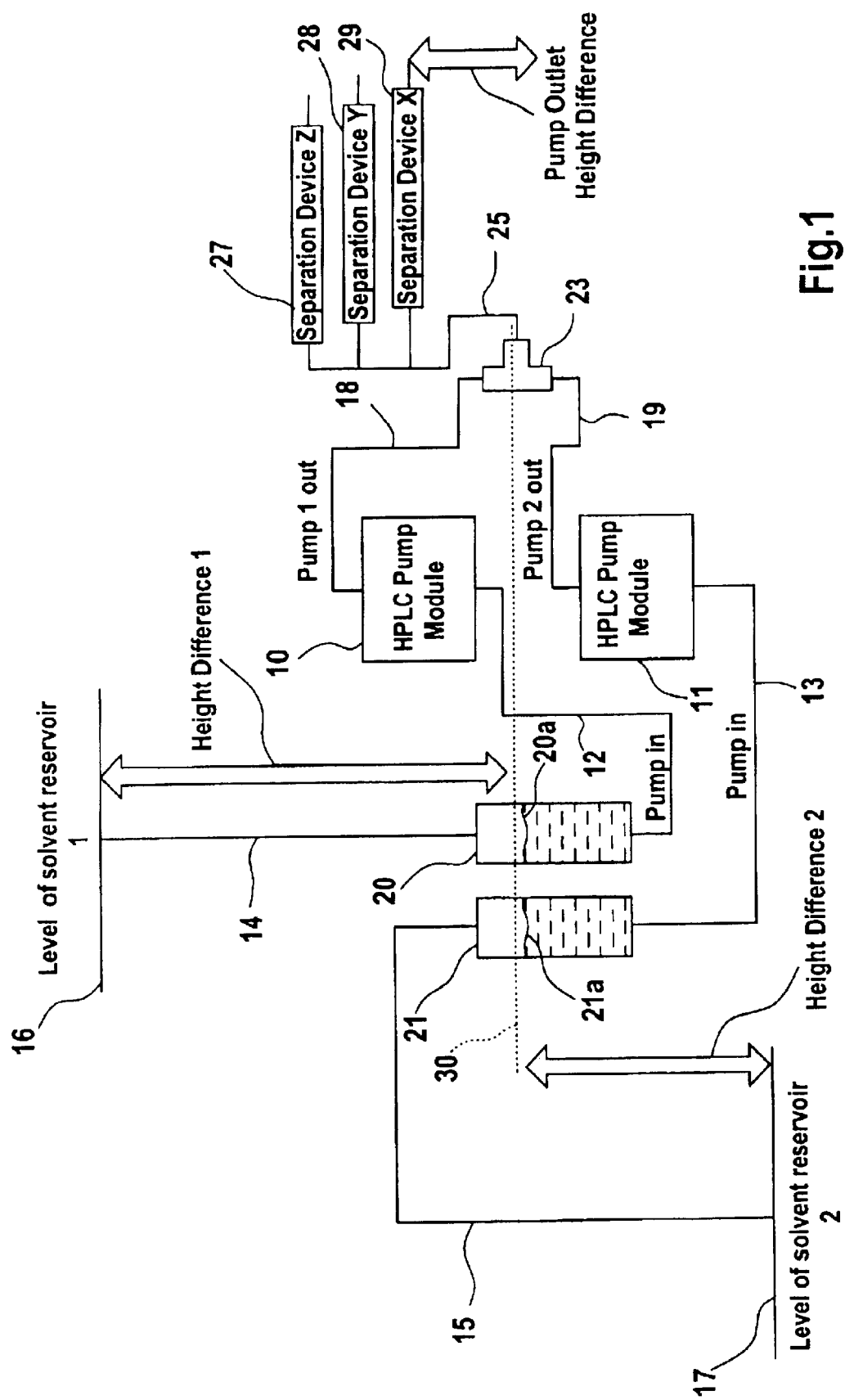
FIG. 1 illustrates an embodiment of a pumping arrangement of the invention.

FIG. 1 shows a preparative HPLC system with two high pressure pump modules 10 and 11 to form solvent gradients. The inlet of the first pump module 10 is connected via a tube 12 to the outlet of a first filtration device 20. The inlet of the filtration device 20 is connected via a tube 14 to a first solvent reservoir. The height level of the first solvent reservoir is indicated at position 16. The inlet of the second pump module 11 is connected via a tube 13 to the outlet of a second filtration device 21. The inlet of the second filtration device is connected via a tube 15 to a second solvent reservoir. The height level of the second solvent reservoir is indicated at position 17. The filtration devices 20, 21 will also be referred to as "filter sink" devices 20,21, respectively.

The outlets of the pump modules 10 and 11 are connected via tubes 18 and 19, respectively, to a T-piece 23, from which a further tube 25 leads to one or several separation devices 27, 28, 29. Arranged between the outlet of the pump modules and the separation devices are suitable mixing and injection means (not shown) for high precision solvent mixing before introducing samples into the pressurized solvent stream.

In the embodiment of FIG. 1, the filtration devices 20 and 21 are identical. They are integrated into an HPLC system by means of a holder device that keeps them at the same height level. The liquid levels in the filtration devices are indicated at 20a and 21a, which coincide essentially with the dotted line 30. The outlet of the T-piece 23 or of any further components, such as the separation device 29, is at the same level or above the liquid levels 20a, 21a, in order to prevent uncontrolled flow at the high pressure side of the pumping arrangement. Theoretically, the outlet at the high pressure side could also be below the level 30, if a resistance is arranged at the outlet which is so high that draining of liquid is prevented.

Figure 2:
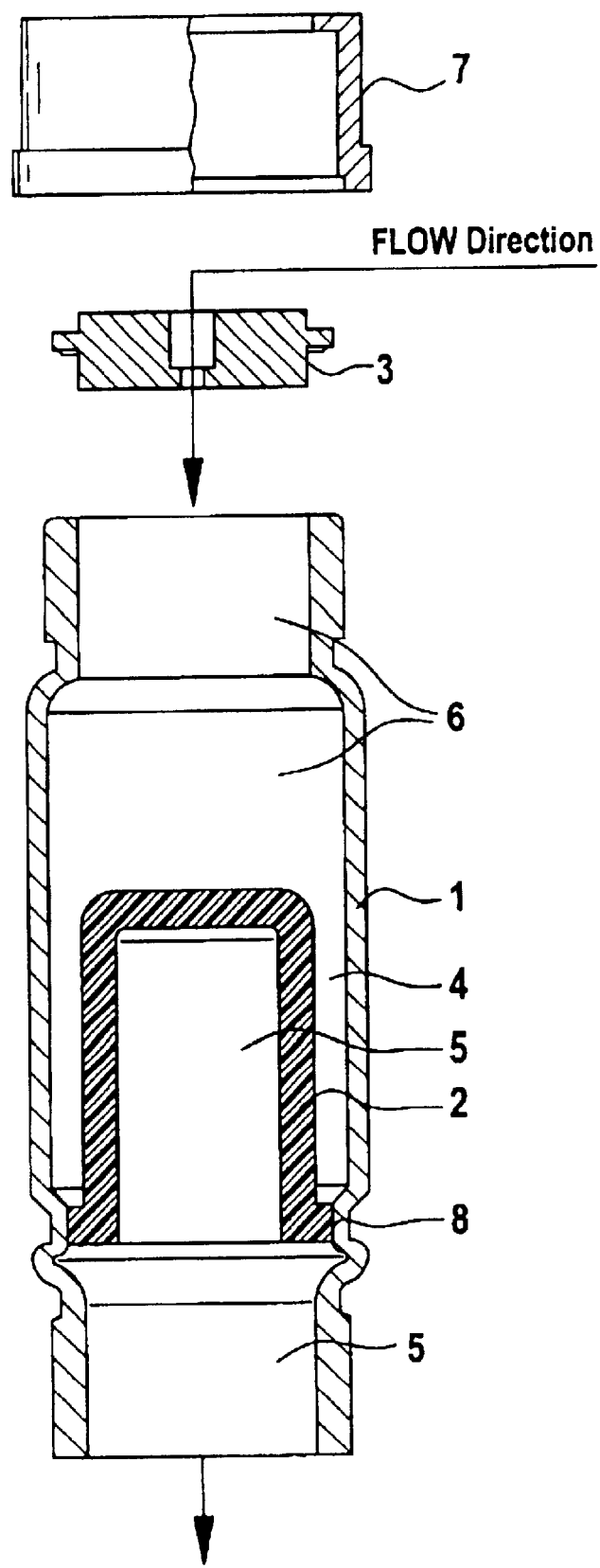
FIG. 2 shows an embodiment of the filtration device used in the pumping arrangement according to FIG. 1.

In the following, the filtration device will be explained in more detail with reference to FIG. 2. The filtration device comprises an outer cylinder 1, which encloses a filtering member 2. The filtering member 2 has a cylindrical shape with a predefined porosity and surface area. It is closed by a bottom at one side.

The housing of the filtering member is hermetically sealed at both ends with two lids 3, each on either side, so that no air, any other gas or liquid will be able to pass through. Each lid has a small tapped hole at its center. The lids allow connecting the filtration device to further devices. In the present embodiment, one of these devices is an HPLC pump module; the other one is a container, filled with solvent. The housing has a predefined spatial orientation. The preferred orientation is bottom upside of the filtering member.

At the outlet side the housing can be connected to the pump module, using a tube. The tube holds a certain inner diameter. The diameter used has to take minimal pressure drop into consideration. The tube itself contains a fitting at both sides that exactly fits into the tapped hole of the chamber's lid 3. The other end is connected to the pump module.

A second tube of the same characteristic is attached to the inlet side of the filtering device. The other end of the tube is connected to the liquid reservoir that contains the liquid to be filtered.

The complete filtering device is split into two different chambers:
One chamber, the outer chamber 4 contains fresh solvent sucked out of the solvent reservoir, the second chamber, the inner chamber 5 contains pre-filtered liquid. The porous filtering member 2 separates the two chambers. Any solvent to be filtered for use is sucked into the apparatus-entering chamber 4, passing the porous filtering member 2 from the outer to the inner area and thus moving into inner chamber 5.

Prior to starting the filtration process the cylindrical device is filled with appropriate liquid up to a predefined level. Typically the liquid level meets the bottom of the filtration device to have full access to the total surface area and filter capacity. All other volume above the bottom of the filtration device remains empty (6). In practice this volume 6 will automatically become saturated by air and/or vapor of the solvent to be filtered. Thus the outer chamber physically contains a 2-phase system, consisting of a liquid phase to be filtered and air or vapor phase of said solvent (6).

A typical version of the described filtration device is made of a borosilicate glass chamber, having two outer threads made of glass. These threads located at the end of both sides provide appropriate sealing of the glass chamber having separate screws 7 on each side. The screws 7 are made out of polymeric material. In each screw an insert or lid 3 is embedded, which is made of PTFE (polytetrafluoroethylene). The insert 3 has a different thread, centered in its center point. This thread is bottomed flat and forms the area for proper sealing with the corresponding tube from the solvent reservoir, as well as to the tube connecting the inlet of the pump module.

Typically the filtering member 2 is a cylindrical sintered glass body which is also made of borosilicate material. The pore size is in the range of 7–10 micrometers. The filtering member 2 and the outer glass cylinder 1 are connected at position 8 by a special melting process. This design allows full access of filter capacity while at the same time the already filtered liquid is kept apart from unfiltered liquid without requiring any additional mechanical seal.

Another advantage of this embodiment consists in the properties of the materials used: no corrosion will occur when oxidizing liquids are delivered. The borosilicate glass as well as PTFE will withstand the complete pH range of solvents that is typically used in HPLC. PTFE is resistant to all solvents typically used in liquid chromatography.

In the following, it will be explained how the present invention also provides a solution to the problem of undesired backflow, for example of mixed solvent into pure solvent stored at a lower storage level.

Referring to FIG. 1, two different situations may occur in practice:
a) The solvent reservoirs are located at the same level compared to the pump modules.
b) The solvent reservoirs are located at different levels compared to the pump modules and to each other.

In all cases the filter sink device in line with the connecting tubes can be seen as an hydraulically communicating system, and the hydrostatic pressure, corresponding to the maximum height difference possible between the solvent reservoirs, has to be considered. The liquid level in the filter sink devices shown in FIG. 1 fulfills the equation $$P = F * s * h$$

Wherein:
P . . . Hydrostatic pressure
F . . . Mechanical force due to height difference
s . . . Specific gravity
h . . . Solvent height in filtration device During normal operation, hydrostatic pressure is of no relevance as the driving force for liquid flow is the adjusted pump flow, created by the motor pump motion. However, in case the pump flow settings are at zero ml/min or if at least one pump motor drive is off, hydrostatic pressure may become the relevant driving force as long as no pressure balance will be achieved. The hydrostatic pressure will force all solvents to the same liquid level (steady state). Then the flow will stop automatically. It applies:

$$F*s*h(\text{Filter sink 1}) = F*s*h(\text{Filter sink 2})$$

As long as the pump valves are sealing properly all solvent will remain in steady state without any flow motion. In case of a small leakage the hydrostatic pressure present will be the driving factor and will provide pressure balance on the low-pressure side. This effect may cause undesired backflow of mixed solvent into pure solvent stored at the lower storage level.

The arrangement according to the invention prevents uncontrolled cross flow by leveling out the hydrostatically caused pressure drop with the design and location of the filter sink (FIG. 1).

Another advantage of the invention refers to handling of non-degassed solvents: Solvents used in analytical HPLC must be degassed prior to use in order to achieve best reproducibility of the separation results. In many high-flow preparative HPLC applications the aspect of using degassed solvents has not played the same important role. Thus, in preparative HPLC applications the solvents used are often non-degassed.

This circumstance favors the formation of tiny little air droplets over time. Very often, they are moved forward and backward within the solvent pipe and finally to the pump inlet. These droplets may increase their size over time and suddenly become sucked into the pump module. Such events cause short irregularities within the pump, resulting in unstable flow.

The filter sink prevents this effect. The filter sink's outer chamber contains a certain volume 6 above the filter bottom portion that is not filled with solvent. This volume can be described physically as a two-phase system: it contains the appropriate liquid to be sucked into the pump and its vapor phase on top of that. The two-phase system allows sucked in air droplets to be collected in the upper vapor phase, before the liquid itself is passing the inner chamber filtration member 2.

Priming high flow HPLC instrumentation is of general importance and is cumbersome whenever the pump to be used exceeds a certain height difference to the level of the liquid to be pumped (FIG. 1). The most critical situation occurs, whenever the pump inlet tube that connects the solvent reservoir to the pump is filled with air, e.g. prior to the set up of an HPLC system with the required solvent reservoirs.

The present invention provides the desired convenience to start immediately without taking care of displacing the air by solvent. Starting the pump will suck in the solvent being stored inside the filter sink. As of pressure equalization the empty tube that connects the solvent reservoir to the filter sink becomes filled with solvent. Typically the vapor phase volume 6 inside the filter sink has the same volume size as the filter sink inlet tube.

In a different embodiment, the filter sink is completely filled with solvent prior to use. The solvent volume 6 will be displaced by the air volume inside the inlet tube at the time the pump device is started. At the same time the inlet tube is filled with the desired solvent sucked out of the connected solvent reservoir.

In the following, alternative embodiments and further developments to those explained above will be described.

The filter capacity of the filter sink can be tailored to specific application needs. This is achieved by either increasing the cross section of the filter and/or the filter length.

The filter performance can be improved further by decreasing the pore size and the pore size distribution. However, when decreasing the pore size the flow resistance will increase and thus a certain amount of partial vacuum within the apparatus will be created. To solve this drawback the pore size has to be matched with the pump characteristics and the preferred liquid to be used.

In another technical solution the inner filtering member 2 has a cylindrical shape with defined porosity, but an impervious bottom. In that case incoming solvent is filtered only at the cylinder walls of the filtering member.

In a further embodiment the borosilicate glass of the outer chamber 1 is colored at its outer surface. This embodiment allows protection against UV radiation caused by normal daylight. The colored coating diminishes the formation of algae whenever water plays a role in the HPLC process. Typically 80 percent of the HPLC applications are performed with a mobile phase comprising a mixture of water and organic solvent.

What is claimed is:

1. A pumping assembly comprising:
   a first liquid reservoir at a first height level, connected via a first hydraulic path to a pumping means;
   a second liquid reservoir at a second height level, connected via a second hydraulic path to the pumping means; and
   first and second filtration devices arranged in the first and second hydraulic path, respectively, wherein each filtration device comprises an outer member forming a first chamber, and an inner member arranged within the outer member and forming a second chamber, with the inner member being porous for allowing liquid flow from the first chamber to the second chamber.

2. The pumping assembly as in claim 1, wherein the pumping means comprises a first pump module connected to the first hydraulic path and a second pump module connected to the second hydraulic path, and wherein the filtration devices are arranged at the same height level.

3. Pumping assembly as in claim 2, wherein the filtration devices are identical.

4. Pumping assembly as in claim 1 wherein the first chamber is designed for accommodating a multi phase system comprising a liquid phase, and a gas phase comprising vapor of the liquid from the first or second liquid reservoirs.

5. Pumping arrangement as in claim 4, wherein the gas phase has a volume of at least 50% of the liquid phase.

6. Pumping assembly as in claim 1, wherein the outer member of the filtration device is formed of borosilicate glass.

7. Pumping assembly as in claim 1, wherein the inner member of the filtration device is formed of sintered borosilicate glass.

8. Pumping assembly as in claim 1, wherein the filtration device comprises an insert made of PTFE-which is arranged at the end of the outer member and which contributes to a sealing connection of the filtration device with a connected tube.

9. Pumping assembly as in claim 1, wherein the volume in the hydraulic path between the liquid reservoir and the filtration device, and the gas volume which can be accommodated in the filtration device are matched such as to allow optimum liquid priming before the pumping operation of the pumping assembly starts.

\* \* \* \* \*